United States Patent
Whitney et al.

(12)

(10) Patent No.: US 6,482,977 B1
(45) Date of Patent: Nov. 19, 2002

(54) MELT PROCESS FOR THE SYNTHESIS OF DIARYL ESTERS OF ALIPHATIC DIACIDS

(75) Inventors: John Morgan Whitney, Niskayuna, NY (US); Rein Mollerus Faber, Bergen op Zoom (NL); Geert Boven, Steenbergen (NL); Jan-Pleun Lens, Breda (NL)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/628,254

(22) Filed: Jul. 28, 2000

(51) Int. Cl.$^7$ .......................... C07C 69/00; C07C 69/34; C07C 69/52
(52) U.S. Cl. .................. 560/221; 560/130; 560/190
(58) Field of Search .................. 560/130, 190, 560/204, 146, 133, 221

(56) References Cited

U.S. PATENT DOCUMENTS 3,553,167 A  * 1/1971  Schnell et al. ............... 260/47

FOREIGN PATENT DOCUMENTS

| DE | 1115252 | 10/1961 |
|----|---------|---------|
| EP | 0044509 A | 1/1982 |
| JP | 55-100339 | * 7/1980 ......... C07C/69/017 |

OTHER PUBLICATIONS

Preparation of Polycarbonate–polyesters, Sakashita, Takeshi et al., (Nihon GE Plastics, Ltd., Japan), Jpn. Kokai Tokkyo Koho (1991), 16 pp. Coden:JKXXAF JP 03203926 A2 199110905 Heisei. Patent written in Japanese. Application: JP 89–340289 19891229. CAN 116:7092 AN 1992:7092 CAPLUS (Copyright 2002ACS).

Database WPI, Section Ch, Week 9631 Derwent Publications Ltd., London, GB: Class A41, AN 1996–303520; XP 002185467 & JP 07 126213 A (Teijin), May 16, 1995.

Chemical Abstracts, vol. 131, No. 25, Dec. 20, 1999, Columbus, OH, US; abstract no. 336796, C.I. Chiriac: "Synthesis of esters with aromatic structure from aromatic carboxylic acids and diphenyl carbonate", p. 650; col. 2; XP00218592 abstract & Rev. Roum. Chim., vol. 43, No. 11, 1998.

* cited by examiner

*Primary Examiner*—Richard L. Raymond
*Assistant Examiner*—Zachary C. Tucker
(74) *Attorney, Agent, or Firm*—Andrew J. Caruso; Noreen C. Johnson

(57) ABSTRACT

This invention relates to a method for preparing diaryl esters, comprising the step of reacting a mixture comprising diaryl carbonate and a dicarboxylic acid, wherein 2.005 to 2.2 molar equivalents of diaryl carbonate per molar equivalent of dicarboxylic acid are provided.

10 Claims, No Drawings

MELT PROCESS FOR THE SYNTHESIS OF DIARYL ESTERS OF ALIPHATIC DIACIDS

FIELD OF THE INVENTION

This invention relates to a method for preparing diaryl esters of aliphatic acids. Diaryl esters of aliphatic diacids are used as monomers in melt polymerization processes for preparing polyestercarbonates.

BACKGROUND OF THE INVENTION

Polycarbonates are well known as tough, clear, highly impact resistant thermoplastic resins. Polycarbonates, however, possess relatively high melt viscosity. The polycarbonate of 4,4'-isopropylidenediphenol (bisphenol A polycarbonate), for instance, is a well know engineering molding plastic.

In order to prepare a molded article from polycarbonate, relatively high extrusion and molding temperatures are required. In order to reduce the melt viscosity while also maintaining the desired physical properties, methods including the addition of plasticizers, the incorporation of aliphatic chainstoppers, the reduction of molecular weight, and the preparation of blends of polycarbonate with other polymers have been practiced.

One method of reducing the melt viscosity while maintaining the desired physical properties of a polymer is the incorporation of residues of aliphatic diacids into the backbone of the polymer chain. These residues are commonly referred to as "soft blocks". Diaryl esters of aliphatic diacids are prepared industrially by two methods: 1) Transesterification with phenyl acetate; 2) Reaction of alkanedioyl dichlorides with phenol.

Some new commercial polycarbonate plants synthesize polycarbonate by a transesterification reaction whereby a diester of carbonic acid (e.g., diarylcarbonate) is condensed with a dihydric compound (e.g., bisphenol-A). This reaction is performed without a solvent, and is driven to completion by mixing the reactants under reduced pressure and high temperature with simultaneous distillation of the phenol produced by the reaction. This synthesis technique is commonly referred to as the "melt" technique. Diaryl esters may be used as monomers in melt polymerization processes to prepare polyestercarbonates. The incorporation of the diaryl esters provides reduced melt viscosity in the polymer, while maintaining the desirable properties of the polycarbonate.

Residual acid contaminates generated by the esterification reactions mentioned above are detrimental to a base-catalyzed melt process used to prepare polyestercarbonates in that the rate of the melt polymerization is decreased. Thus, the diaryl ester monomer must be purified. The purification involves multiple recrystallization steps in solvents. The purification steps add considerable cost to the preparation of the diaryl ester monomers.

It would be desirable to prepare diaryl esters of aliphatic diacids that do not require extensive purification before introduction into a melt process. In particular, it would be desirable to prepare diaryl esters of aliphatic di acids that have a sufficiently low level of acids impurities such that the diaryl esters may be introduced into a melt process without requiring purification steps.

BRIEF SUMMARY OF THE INVENTION

In one aspect, the invention relates to a method for preparing diaryl esters suitable for use in a melt transesterification process, comprising the step of reacting a diaryl carbonate and a dicarboxylic acid in the presence or absence of a base, wherein from 2.005 to 2.2 molar equivalents of diaryl carbonate per molar equivalent of dicarboxylic acid are provided. In one embodiment, the diaryl esters contain less than 10 ppm of residual carboxylic acids.

In a further aspect, the invention relates to a method for preparing polyestercarbonate by the melt process utilizing the diaryl esters prepared by reacting a diaryl carbonate and a dicarboxylic acid, wherein from 2.01 to 2.02 molar equivalents of diaryl carbonate per molar equivalent of dicarboxylic acid are provided.

DETAILED DESCRIPTION OF THE INVENTION

The present invention may be understood more readily by reference to the following detailed description of preferred embodiments of the invention and the examples included therein.

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In the following specification, reference will be made to a number of terms that shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "melt polycarbonate" refers to a polycarbonate made by the transesterification of a carbonate diester with a dihydroxy compound.

"BPA" is herein defined as bisphenol A or 2,2-bis(4-hydroxyphenyl)propane.

"SBI" is herein defined as 6,6'-dihydroxy-3,3,3',3'-tetramethylspirobiindane.

"CD-1" is herein defined as 6-hydroxy-1-(4'-hydroxyphenyl)-1,3,3-trimethylindane.

"BCC" is herein defined as 1,1-bis(4-hydroxy-3-methylphenyl)cyclohexane

"DPC" as used herein is defined as diphenyl carbonate.

The terms "diphenol" and "dihydric phenol" as used herein are synonymous.

I. Preparation of Diarylesters

In one aspect, the present invention relates to a method of preparing diaryl esters of aliphatic diacids. The diaryl esters are prepared by the transesterification reaction of a diarylcarbonate and an aliphatic diacid.

The diaryl carbonate is a carbonate diester of an aromatic monohydroxy compound, which is represented by formula (I):

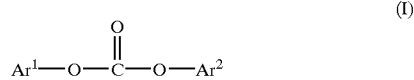

wherein each of $Ar^1$ and $Ar^2$ each independently represents a monovalent carbocyclic or heterocyclic aromatic group; preferably having from 5 to 12 carbon atoms.

Each of the monovalent aromatic groups $Ar^1$ and $Ar^2$ may be unsubstituted or substituted with at least one substituent which does not adversely affect the reaction. Examples of such substituents include, but are not limited to, a halogen atom, a lower alkyl group, a lower alkoxy group, a phenyl group, a phenoxy group, a vinyl group, a cyano group, an ester group, an amide group and a nitro group. Representative examples of monovalent aromatic groups include a phenyl group, a napthyl group, a biphenyl group and a pyridyl group, each of which is substituted or unsubstituted with at least one substituent, as mentioned above.

Representative examples of diaryl carbonates include diphenyl carbonates represented by formula (II)

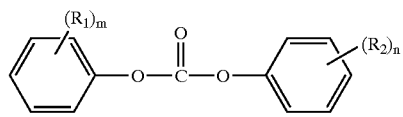
(II)

wherein each of $R_1$ and $R_2$ independently represents a hydrogen atom; a halogen atom; a lower alkyl group; a lower alkoxy group; a cycloalkyl group having from 5 to 10 ring carbon atoms or a phenyl group, and each of m an n independently represents an integer of from 1 to 5; with the proviso that when m is an integer of from 2 to 5, each $R_1$ may be the same or different; and when n is an integer from 2 to 5, each $R_2$ may be the same or different.

Of the diphenyl carbonates represented by formula (II), it is preferable that the diphenyl carbonates have a symmetrical structure; such as diphenyl carbonate; ditolyl carbonate and diphenyl carbonate substituted with a lower alkyl group having from 1 to 4 carbon atoms. In one embodiment, diphenyl carbonate, having formula (III) is used.

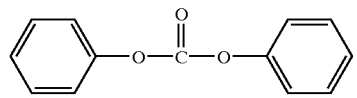
(III)

In the method of the present invention, a transesterification reaction between the diaryl carbonate and an aliphatic diacid, also referred to herein as a "dicarboxylic acid" is conducted to produce diaryl esters. The aliphatic diacid is represented by the general formula (IV):

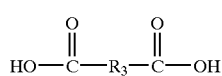
(IV)

wherein $R_3$ is a $C_1$–$C_{40}$ branched or unbranched alkyl or branched or unbranched cycloalkyl.

Representative acids of structure (IV) include, but are not limited, to dodecanedioic acid, sebacic acid, adipic acid, octadecanedioic acid, octadec-9 enedioic acid, 9-carboyxoctadecanoic acid and 10-carboxyoctadecanoic acid. Dodecanedioic acid (DDDA) is the more preferred.

The present invention provides a process whereby diaryl esters are produced having suitable purity for introduction into a subsequent melt polymerization to prepare polyestercarbonates, without requiring extensive purification. In particular, diaryl esters are produced having less than about 0.01 wt percent of free carboxylic acids, based upon the weight of the reaction product and assuming that no phenol is distilled. It is preferable that the product reaction mixture contain less than about 500 ppm residual acid; more preferably less than 100 ppm residual acid; even more preferably less than about 10 ppm residual acid.

In order to obtain a reaction product having the specifications identified above, the reaction is conducted with a stoichiometric excess of diarylcarbonate; in particular from about 2.001 to about 3, more preferably 2.005 to 2.2, even more preferably from about 2.005 to about 2.1 molar equivalents of diaryl carbonate per molar equivalent of dicarboxylic acid are provided during the course of the reaction. In the present invention, it is undesirable to have residual carboxylic acid groups in the product. Residual carboxylic acid groups interfere with the base catalyzed process to prepare polyestercarbonates.

The reaction of the carboxyl groups of the dicarboxylic acid with the diarylcarbonate is optionally accompanied by the elimination of the aromatic hydroxy compound from which the diarylcarbonate was formed, and carbon dioxide. To remove the hydroxy compounds from the reaction mixture, it is heated at reduced pressure, after the reaction is underway. Alternatively, the aromatic compound may remain in the reaction, where it is eventually removed in a wash step, with methanol, for example.

The reaction may be conducted in the presence or the absence of a base catalyst. If a base catalyst is used, the reaction proceeds at a faster rate, however the reaction product will have more impurities. Suitable base catalysts include, but are not limited to tertiary amines such as triethylamine, quaternary phosphonium compounds such as tetraphenylphosphonium tertaphenylborate, quaternary ammonium compounds such as tetramethylammonium hydroxide, hexaalkyl guanidinium halides such as hexaethyl guanidium chloride, alkali or alkaline earth metal hydroxides, and the like. In typical embodiments quaternary ammonium hydroxides are used a preferred base. The base is preferably used in an amount less than $2 \times 10^{-4}$ molar equivalents, based on the aliphatic dicarboxylic acid. If the reaction is conducted in the absence of a base, the process is conducted in an identical manner. The rate of reaction is slower, however the product will have a higher purity.

The reaction is typically conducted by combining the diarylcarbonate and the dicarboxylic acid in the aforementioned ratios, and optionally the base catalyst, at a temperature at from about 180° C. to about 220° C., preferably at about 200° C. Vigorous evolution of carbon dioxide ensues after all components have melted. Optionally, a moderate vacuum is applied to distill the monohydroxyaromatic compound, for example phenol, from the melt.

In an alternative embodiment, the transesterification may be conducted in a solvent. Any inert solvent having a boiling point above about 120° C., more preferably above about 180° C. is suitable. Examples of suitable solvents include, but are not limited to phenols; polyethylene glycols; polyaromatic compounds; hydrocarbon oils and mixtures thereof. In one embodiment, phenol is used as a solvent as it is already created during the transesterification reaction and can be easily removed by precipitation or distillation. The solvent may comprise from about 0.1 to about 10 parts by weight, of the initial reaction composition, based on the total weight of the reaction composition; more preferably from about 1 to about 3 parts by weight of the initial reaction composition.

The reaction can be conducted as a batch or a continuous process. Any desired apparatus can be used for the reaction. The material and the structure of the reactor used in the present invention is not particularly limited as long as the reactor has an ordinary capability of stirring It is preferable to have an inert gas supply and vacuum.

Optionally, after the transesterification of the diaryl carbonate and the dicarboxylic acid, the reaction product may be further purified to remove residual diaryl carbonate and acid. In one embodiment, the reaction product is dissolved in from about 1 to about 3 weight equivalents of an organic solvent. Suitable organic solvents include, but are not limited to methanol; and a methanol/methylene chloride solution.

The reaction mixture is typically cooled to from about 40 to about 60° C. and the organic solvent is added. The mixture is typically heated up to about 60° C. until no solids are observed. Thereafter, the solution is chilled to a temperature of from about 0 to about 5° C. which results in the precipitation of crystals of the diaryl ester of the diacids. The precipitate may be filtered and washed at ambient temperature with an organic solvent, for example methanol, to obtain the product as a white flaky solid.

The diaryl ester may be used in the same plant after being made, stored for later use, or packaged for transport, all in commercial quantities. In one embodiment, the diaryl ester is introduced directly into a melt process for the preparation of polyestercarbonate.

II. Melt Process Using Diarylesters as Monomers

In a second aspect, the invention relates to the use of the diarylesters prepared according to the method outlined in section I of the specification in a melt polymerization process in which dihydric phenol and a diester of carbonic acid are reacted along with the diarylester, which is incorporated into the backbone of the polymer. Residues of dihydric phenols which are useful in preparing the polyestercarbonate the invention may be represented by the general formula (V):

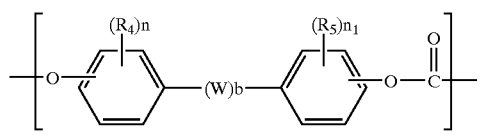

(V)

wherein:
R$_4$ is independently selected from halogen, monovalent hydrocarbon, and monovalent hydrocarbonoxy radicals;
R$_5$ is independently selected from halogen, monovalent hydrocarbon, and monovalent hydrocarbonoxy radicals:
W is selected from divalent hydrocarbon radicals,

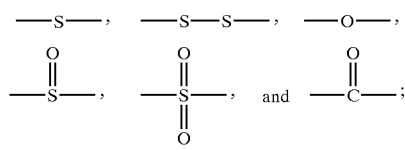

n and n$^1$ are independently selected from integers having a value of from 0 to 4 inclusive; and
b is either zero or one.

The monovalent hydrocarbon radicals represented by R$_4$ and R$_5$ include the alkyl, cycloalkyl, aryl, aralkyl and alkaryl radicals. The preferred alkyl radicals are those containing from 1 to about 12 carbon atoms. The preferred cycloalkyl radicals are those containing from 4 to about 8 ring carbon atoms. The preferred aryl radicals are those containing from 6 to 12 ring carbon atoms, i.e., phenyl, naphthyl, and biphenyl. The preferred alkaryl and aralkyl radicals are those containing from 7 to about 14 carbon atoms.

The preferred halogen radicals represented by R$_4$ and R$_5$ are chlorine and bromine.

The divalent hydrocarbon radicals represented by include the alkylene, alkylidene, cycloalkylene and cycloalkylidene radicals. The preferred alkylene radicals are those containing from 2 to about 30 carbon atoms. The preferred alkylidene radicals are those containing from 1 to about 30 carbon atoms. The preferred cycloalkylene and cycloalkylidene radicals are those containing from 6 to about 16 ring carbon atoms.

The monovalent hydrocarbonoxy radicals represented by may be represented by the formula—OR$^2$ wherein R$^2$ is a monovalent hydrocarbon radical of the type described hereinafore. Preferred monovalent hydrocarbonoxy radicals are the alkoxy and aryloxy radicals.

Suitable dihydric phenols include, but are not limited to, BPA; 2,2-bis(3,5-dibromo-4-hydroxyphenyl)propane; 2,2-bis(3,5-dimethyl-4-hydroxyphenyl)propane; 1,1-bis(4-hydroxyphenyl)cyclohexane; 1,1-bis(3,5-dimethyl-4-hydroxyphenyl)cyclohexane; 1,1-bis(4-hydroxyphenyl) decane; 1,1-bis(4-hydroxyphenyl)propane; 1,1-bis(4-hydroxyphenyl)cyclodecane; 1,1-bis(3,5-dimethyl-4-hydroxyphenyl)cyclododecane; 4,4-dihydroxyphenyl ether; 4,4-thiodiphenol; 4-4-dihydroxy-3,3-dichlorodiaryl ether; 4,4-thiodiphenol; 4,4-dihydroxy-3,3-dichlorodiaryl ether; 4,4-dihydroxy-2,5-dihydroxydiaryl ether; BPI; 1,1-bis(4-hydroxyphenyl)-1-phenylethane; 1,1-bis(3-methyl-4-hydroxyphenyl)-1-phenylethane, and mixtures thereof. In one embodiment, the residues of dihydric phenol in the polycarbonate comprise 100 mol % of residues derived from BPA.

Optionally, polyfunctional compounds may be utilized. Suitable polyfunctional compounds used in the polymerization of branched polycarbonate include, but are not limited to, 1,1,1-tris(4-hydroxyphenyl)ethane,
4-[4-[1,1-bis(4-hydroxyphenyl)-ethyl]-dimethylbennzyl],
trimellitic anhydride,
trimellitic acid, or their acid chloride derivatives.

It is also possible to employ residues of two or more different dihydric phenols having the general structure (V) defined above to form co- and terpolymers. In addition to the residues of dihydric phenols having the formula (V) as defined above, residues of dihydric phenols having formulas (VI), (VII), (VIII) or a mixture thereof may be used to prepared co- or terpolymers.

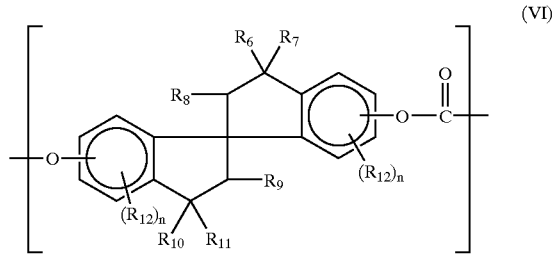

(VI)

where R$_6$, R$_7$, R$_{10}$ and R$_{11}$ are independently C$_1$–C$_6$ alkyl, R$_8$ and R$_9$ are independently H or C$_1$–C$_5$ alkyl, $R_{12}$ is H or $C_1-C_3$ alkyl and n is 0, 1 or 2;

(VII)

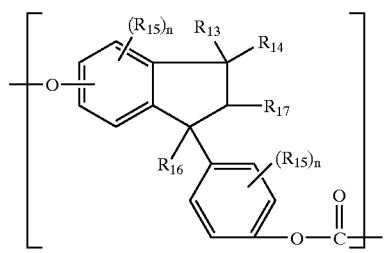

where $R_{13}, R_{14}$ and $R_{16}$ independently represent $C_1-C_6$ alkyl,
$R_{15}$ is H or $C_1-C_3$ alkyl and n is 0, 1 or 2,
$R_{17}$ is H or $C_1-C_5$ alkyl; and (VIII)

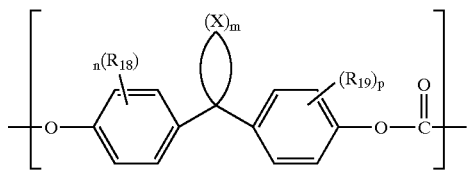

where $R_{18}$ and $R_{19}$ are independently selected from the group consisting of $C_1-C_6$ alkyl;
X represents $CH_2$;
m is an integer from 4 to 7;
n is an integer from 1 to 4; and
p is an integer from 1 to 4
with the proviso that at least one of $R_{18}$ and $R_{19}$ is in the 3 or 3' position.

Representative units of structure (VI), include, but are not limited to residues of 6,6'-dihydroxy-3,3,3',3'-tetramethyl spirobiindane(SBI); 6,6'-dihydroxy-3,3,5,3',3',5'-hexamethyl spirobiindane; 6,6'-dihydroxy-3,3,5,7,3',3', 5',7'-octamethylspirobiindane; 5,5'-diethyl-6,6'-dihydroxy 3,3,3',3'-tetramethylspirobiindane (diethyl SBI) and mixtures thereof. Residues of SBI and its ortho alkylated homologs, and diethyl SBI are most preferred as component (VI).

Representative units of structure (VII) include, but are not limited to residues of 6-hydroxy-1-(4'-hydroxyphenyl)-1,3,3-trimethylindane (CD-1); 6-hydroxy-1-(4'-hydroxy-3'-methylphenyl)-1,3,3,5-tetramethylindane. Residues of CD-1 are most preferred.

Representative units of structure (VIII) include, but are not limited to residues 1,1-bis(4-hydroxy-3-methylphenyl) cyclohexane (B CC); 1,1-bis(4-hydroxy-3-methylphenyl) cyclopentane; 1,1-bis(4-hydroxy-3-methylphenyl) cycloheptane and mixtures thereof. Residues of BCC (structure IX) are most preferred.

(IX)

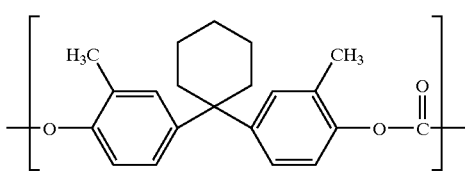

As the diester of carbonic acid, various compounds may be used, including, but not limited to diaryl carbonate compounds, dialkyl carbonate compounds and alkylaryl carbonate compounds. Suitable diesters of carbonic acid include, but are not limited to, diaryl carbonate; bis(4-t-butylphenyl)carbonate; bis(2,4-dichlorophenyl)carbonate; bis(2,4,6-trichlorphenyl)carbonate; bis(2-cyanophenyl) carbonate; bis(o-nitrophenyl)carbonate; ditolyl carbonate; m-cresol carbonate; dinaphthyl carbonate; bis(diaryl) carbonate; diethylcarbonate; dimethyl carbonate; dibutyl carbonate; dicyclohexyl carbonate; and mixtures thereof. Of these, diaryl carbonate is preferred. If two or more of these compound are utilized, it is preferable that one is diaryl carbonate.

Diphenyl carbonates used to make the polyestercarbonates by melt: Suitable carbonate sources, catalysts and reaction conditions are found in U.S. Pat. No. 5,880,248, and *Kirk-Othmer Encyclopedia of Chemical Technology*, Fourth Edition, Volume 19, pp. 585–600, herein incorporated by reference.

In the process of the present invention, an endcapping agent may optionally be used. Suitable endcapping agents include monovalent aromatic hydroxy compounds, haloformate derivatives of monovalent aromatic hydroxy compounds, monovalent carboxylic acids, halide derivatives of monovalent carboxylic acids, and mixtures thereof.

Suitable endcapping agents include, but are not limited to phenol, p-tert-butylphenol; p-cumylphenol; p-cumylphenolcarbonate; undecanoic acid, lauric acid, stearic acid; phenyl chloroformate, t-butyl phenyl chloroformate, p-cumyl chloroformate, chroman chloroformate, hydrocardanol, nonyl phenol, octyl phenol; nonyl phenyl chloroformate or a mixture thereof. Furthermore, mixed carbonates and esters composed of endcappers from the list above along with phenol or alkylsalicylates are acceptable.

If present, the endcapping agent is preferably present in amounts of about 0.01 to about 0.20 moles, preferably about 0.02 to about 0.15 moles, even more preferably about 0.02 to about 0.10 moles per 1 mole of the dihydric phenol.

Typical catalysts employed in the melt condensation polymerization process include, but are not limited to, alkali metal compounds, alkaline earth metal compounds, quaternary ammonium compounds, quaternary phosphonium compounds and combinations thereof.

Useful alkali metal compounds as catalysts include sodium hydroxide, potassium hydroxide, lithium hydroxide, sodium hydrogencarbonate, potassium hydrogencarbonate, lithium hydrogencarbonate, sodium carbonate, potassium carbonate, lithium carbonate, sodium acetate, potassium acetate, lithium acetate, sodium stearate, potassium stearate, lithium stearate, sodium borohydride, lithium borohydride, sodium borophenolate, sodium benzoate, potassium benzoate, lithium benzoate, disodium hydrogenphosphate, dipotassium hydrogenphosphate, dilithium hydrogenphosphate, disodium, dipotassium and dilithium salts of BPA and sodium, potassium, and lithium salts of phenol.

Useful alkaline earth metal compounds as catalysts include calcium hydroxide, barium hydroxide, magnesium hydroxide, strontium hydroxide, calcium hydrogen carbonate, barium hydrogencarbonate, magnesium hydrogencarbonate, strontium hydrogencarbonate, calcium carbonate, barium carbonate, magnesium carbonate, strontium carbonate, calcium acetate, barium acetate, magnesium acetate, strontium acetate, calcium stearate, barium stearate, magnesium stearate, and strontium stearate.

Useful quaternary ammonium compounds as catalysts include tetraalkylammonium compounds such as tetramethylammonium hydroxide and tetraethylammonium hydroxide. Examples of quaternary ammonium compounds include, but are not limited to, tetramethylammonium hydroxide (TMAH); tetraethylammonium hydroxide; tetrabutylammonium hydroxide;
trimethylbenzylammonium hydroxide and mixtures thereof. Examples of suitable quaternary phosphonium compounds include, but are not limited to, tetramethylphosphonium hydroxide; tetraethylphosphonium hydroxide; tetrabutylphosphonium hydroxide and mixtures thereof.

Preferred catalysts include tetramethylammonium hydroxide, sodium hydroxide and mixtures thereof.

The preferred polyestercarbonates have a weight average molecular weight of about 5,000 to about 100,000, more preferably of about 10,000 to about 65,000, and most preferably about 18,000 to about 36,000 as measured by gel permeation chromatography versus polystyrene standards.

The reaction conditions of the melt polymerization are not particularly limited and may be conducted in a wide range of operating conditions. The reaction temperature is typically in the range of about 100 to about 350° C., more preferably about 180 to about 310° C. The pressure may be at atmospheric, or at an added pressure of from atmospheric to about 15 torr in the initial stages of the reaction, and at a reduced pressure at later stages, for example in the range of about 0.2 to about 15 torr. The reaction time is generally about 0.1 hours to about 10 hours.

The melt polymerization may be accomplished in one or more stages, as is known in the art. In one embodiment, the process is conducted as a two stage process. In the two stage process, the first stage is an oligomerization stage, and the second stage is a polymerization stage. In the first stage of this embodiment, the base, for example the quaternary ammonium or phosphonium compound, is introduced into the reaction system comprising the dihydroxy compound and the carbonic acid diester and the diarylester. The first stage is conducted at a temperature of 290° C. or lower, preferably 150 to 290° C., more preferably 200 to 280° C. The duration of the first stage is preferably 0 to 5 hours, even more preferably 0 to 3 hours at a pressure from atmospheric pressure to 100 torr, with a nitrogen atmosphere preferred. Alternatively, the base may be introduced prior to the first stage, in a monomer mix tank, for instance. The contents from the monomer mix tank are fed to the first stage., or anywhere in between. The molecular weight of the oligomer is less than 8,000 Mn.

The base catalyst is typically present in a range between about $10^{-8}$ moles and about $10^{-3}$ moles to moles of aromatic dihydroxy compound. In another embodiment, the catalyst is present in a range between about $10^{-7}$ moles and about $10^{-5}$ moles to moles of aromatic dihydroxy compound.

Additives may also be added to the polycarbonate product as long as they do not adversely affect the properties of the product. These additives include a wide range of substances that are conventionally added to the polycarbonates for a variety of purposes. Specific examples include heat stabilizers, epoxy compounds, ultraviolet absorbers, mold release agents, colorants, antistatic agents, slipping agents, anti-blocking agents, lubricants, antifogging agents, natural oils, synthetic oils, waxes, organic fillers, flame retardants, inorganic fillers and any other commonly known class of additives.

The reaction can be conducted as a batch or a continuous process. Any desired apparatus can be used for the reaction. The material and the structure of the reactor used in the present invention is not particularly limited as long as the reactor has an ordinary capability of stirring. It is preferable that the reactor is capable of stirring in high viscosity conditions as the viscosity of the reaction system is increased in later stages of the reaction.

EXAMPLES

The following examples are set forth to provide those of ordinary skill in the art with a complete description of how the compositions of matter and methods claimed herein are made and evaluated, and are not intended to limit the scope of what the inventors regard as their invention. Efforts have been made to insure accuracy with respect to numbers (e.g., amounts, temperature, etc.) but some errors and deviations should be accounted for. Unless indicated otherwise, parts are by weight, temperature is in ° C.

Molecular weights are reported as weight average ($M_w$), unless otherwise noted, and were determined by GPC analysis of polycarbonate prepared by melt polymerization. Standards of polystyrene were used to construct a universal calibration against which polycarbonate could be measured using the Mark-Houwink equation. The temperature of the columns was 25° C. and the mobile phase was chloroform.

Example 1

(No Base)

1,10-decanedioic acid (192 g, 0.95 mol) was combined with diphenyl carbonate (417 g, 1.95 mol) in a 3 neck round bottom flask equipped with a mechanical stirrer, reflux condenser, and heating mantel. An argon atmosphere was maintained over the reactants during the course of the reaction. The components were melted and kept between 200 to 220 C. Carbon dioxide evolution is observed for 4–6 hours. When carbon dioxide evolution ceased, the molten products were cooled to 40–60 C and methanol was added (1–3 weight equivalents) and the mixture was stirred and heated to 60 C until no solids were observed. The solution was slowly chilled to 0–5 C at which point crystals of the diphneyl ester of the diacid precipitated. The precipitate was filtered and washed with ambient temperature methanol (1–3 weight equivalents) to obtain the product as a white flaky solid. The solid was dried in a vacuum oven for 12 hours at 40–60 C. Analysis of the solid by proton nuclear magnetic resonance ($^1$H-NMR) and gas chromatograph mass spectrometry (GCMS) showed the material to be >98% pure diphenyl 1,10-decanedioate diester (281 g, 83% yield). Note: Upon standing, the methanol will produce further crystalline diphenyl 1,10-decanedioate diester which can be isolated by filtration to achieve close to theoretical yield.

Example 2

(No Base)

1,18-octadecanedioic acid (149.5 g, 0.475 mol) was combined with diphenyl carbonate (208.77 g, 0.975 mol) in a 3 neck round bottom flask equipped with a mechanical stirrer, reflux condenser, and heating mantel. An argon atmosphere was maintained over the reactants during the course of the reaction. The components were melted and kept between 200 to 220 C. Carbon dioxide evolution was observed for 12–16 hours. When carbon dioxide evolution ceased, the molten products were cooled to 40–60 C and a methanol/methylene chloride (3:1) solution was added (1–3 weight equivalents) and the mixture was stirred and heated to 60 C until no solids were observed. The solution was slowly chilled to 0–5 C at which point crystals of diphenyl ester of the diacid precipitated. The precipitate was filtered and washed with ambient temperature methanol (1–3 weight equivalents) to obtain the product as white flaky solid. The solid was dried in a vacuum oven for 12 hours at 40–60 C.

Analysis of the solid by $^1$H-NMR and GCMS show the material to be >98% pure diphenyl 1,18-octadecanedioate diester (183 g, 83% yield). Note: Upon standing, the methanol/methylene chloride solution will produce further crystalline diphenyl 1,18-octadecanedioate diester which can be isolated by filtration to achieve close to theoretical yield.

Example 3
(With Base)

1,12-Dodecanedioic acid (5.12 g, 22.2 mmol) was combined with diphenyl carbonate (10 g, 46.7 mmol) and basic catalyst, (hexaethylguanidium)$_3$(BPA)$_2$(0.0045g, 4×10–6 mol), at 200 C. Vigorous carbon dioxide evolution ensued after all components had melted. The temperature was increased to 250 C while pulling a moderate vacuum to distill phenol from the melt. After 4 hours, GCMS confirmed >98% conversion to the desired diphenyl ester. The product was water-white.

Example 4
(With Base)

1,12-Dodecanedioic acid (6.2933 g, 27.3 mmol) was combined with diphenyl carbonate (17.5556 g, 82 mmol) and tetramethylammonium hydroxide (0.3 g of a 25 wt % solution in water, 0.82 mmol) in a round flask equipped with a nitrogen inlet and reflux condenser (heated at 45° C.). The powder mixture was flushed with nitrogen long enough to remove all oxygen. Then the flask was immersed into an oil bath at 210° C. Carbon dioxide evolved during the course of the reaction. After 5 hours full conversion was reached (or 3 hours at 230° C.). The reaction mixture was cooled to 150° C. and phenol was distilled off under reduced pressure. The reaction mixture was cooled to 80° C. at which point methanol (460 g) was added carefully. The solution was allowed to cool down and stored overnight at 5° C. White crystals were formed, isolated by means of vacuum filtration and dried during 2 hours at 60° C. under vacuum. $^1$H-NMR showed full conversion to the diphenyl ester derivative.

Example 5
(With Base)

1,12-Dodecanedioic acid (1173 g, 5.09 mol) was added to molten (3275 g, 15.29 mol) diphenyl carbonate at 150° C. in an oil-jacketed glass continuous stirred tank reactor (CSTR) equipped with a reflux condenser (at 60° C.) and allowed to melt. 2 kgs of the mixture was pumped into a second oil-jacketed glass CSTR at 150° C. Tetramethylammonium hydroxide (11.6 ml of a 25% aq, 0.0319 mol) was slowly added to the reaction mixture. CO$_2$ gas evolved immediately. The temperature was raised to 230° C. over 2 hours. The reaction was completed after 2 hours at 230° C. (part of the phenol distilling off). Purification of the reaction product was performed as described in previous examples. $^1$H-NMR showed full conversion to the diphenyl ester.

Example 6
(With Base)

A mixture of PRIPOL 1009 (C36 dimer acid, provided by UNIQEMA; 12.6 g, 0.022 mole), diphenyl carbonate (DPC; 14.4 g, 0.067 mole), and tetramethylammonium hydroxide (250 microliters, 2.74 M aq. solution) was heated up to 220° C. After stirring for 8 hours, the reaction mixture was cooled to room temperature.

Subsequently, phenol and excess DPC were removed by vacuum distillation. $^1$H-NMR showed full conversion to the diphenyl ester.

Example 7
(With Base)

A mixture of a carboxylic acid end capped polyester based on PRIPOL 1009 (C36 dimer acid), adipic acid and neopentyl glycol (UCN 99.195, manufactured by UNIQEMA; 18.1 g, 0.014 mole), diphenyl carbonate (8.9 g, 0.042 mole), and tetramethylammonium hydroxide (155 microliters, 2.74 M) was heated up to 220° C. After stirring for 8 hours, the reaction mixture was cooled to room temperature. Subsequently, phenol and excess DPC were removed by vacuum distillation. $^1$H-NMR showed full conversion to the diphenyl ester.

Example 8

This example demonstrates a batch procedure for preparation of polyestercarbonate using diarylesters prepared according to the method of the invention.

In a jacketed glass reactor equipped with an overhead stirrer and connecting distillation trap, diphenyl carbonate (256.81 g, 1.199 moles), bisphenol-A (234.368 g, 1.027 moles), and the diphenyl ester of 1,18-octadecanedioic diacid (29.498 g, 0.063 moles) were combined. Catalyst solutions were then injected (1090 microliters of 0.001 M aq. sodium hydroxide and 272 microliters of 1.0 M aq. tetramethylammonium hydroxide). The reactor was repeatedly evacuated and refilled with nitrogen until the oxygen content was substantially minimized (preferably below 100 ppm). The monomers were melted and stirred for 30 minutes from 140 to 180 C, under nitrogen. Then, over the course of 210 minutes, the temperature was raised to 310 C and the vacuum lowered to 1.5 millibar. Phenol was observed to distill out of the reactor into the chilled trap throughout the polymerization. The reactor was repressurized with nitrogen and the molten polymer expelled (290 g). It was observed by H-NMR that the theoretical amount of 1,18-octadecanedioic diacid had been incorporated. The weight average molecular weight of the material was 26,634 and the Tg is 113.5 C.

Example 9

This example demonstrates the use of diphenyl 1,12-dodecanedioic diester (DDDA-DPE) derived from DPC transesterification method in a continuous melt reactor to prepare a polyestercarbonate.

A monomer mix drum was charged continuously with DPC, BPA, and DDDA-DPE such that the molar ratios were (respectively) 11.41:11.56:1. The temperature of the drum was maintained at 170 C under 1 bar of nitrogen. The molten monomer mixture was fed continuously at 3 kg/hour into a vertical stirred reactor heated at 225 C with a vacuum of 170 mbar. Additionally, a catalyst solution comprised of aqueous NaOH (5.0×10–6 mol/mol BPA) and TMAH (5.0×10–4 mol/mol BPA) was continuously fed into the reactor. The residence time in this first reactor was approximately 40 minutes. The partially oligomerized material was next fed into a second vertical stirred reactor heated at 260 C with a vacuum of 30 mbar. The residence time in this reactor was approximately 30 minutes. Polymer (of approximately 5,000 Mw) was delivered from the second reactor into a final horizontal polymerizer. The polymerizer was heated to 300 C with a vacuum of 4 mbar. The residence time was approximately 90 minutes in the polymerizer. Resin was delivered at a rate of 1.8 kg/hour from the polymerizer to a pelletizer. Analysis of the pelletized resin by H-NMR was consistent with a copolymer comprised of about 8% DDDA units. The molecular weight (Mw) of the resin as determined by GPC (PS standards) was 38.4 kg/mol. DSC analysis for glass transition temperature (Tg) was 124 C.

This invention has been described in detail with particular reference to preferred embodiments thereof, but it will be understood that variations and modifications can be effected within the spirit and scope of the invention.

What is claimed is:

1. A method for preparing diaryl esters, said method comprising:
    (a) reacting a mixture comprising a diaryl carbonate and an aliphatic dicarboxylic acid to afford a reaction product, said mixture comprising 2.005 to 2.2 moles of diaryl carbonate per mole of aliphatic dicarboxylic acid;
    (b) cooling the reaction product and thereafter dissolving the reaction product with a solvent, thereby forming a solution; and
    (c) cooling the solution to precipitate a product comprising purified diaryl esters.

2. The method of claim 1, further comprising the step of distilling volatile components from the reaction mixture during the reaction of the diaryl carbonate and the dicarboxylic acid.

3. The method of claim 2 wherein the volatile components are phenol and diphenyl carbonate.

4. The method of claim 1, further comprising the step of introducing a base catalyst into the mixture said base being present in an amount less than $2 \times 10^{-4}$ moles of base per mole of aliphatic dicarboxylic acid.

5. The method according to claim 4 where the base catalyst is a quaternary ammonium compound, an alkali metal compound, an alkaline earth metal compound or combination thereof.

6. The method of claim 5, wherein the catalyst is tetramethylammonium hydroxide, sodium hydroxide or combinations thereof.

7. The method of claim 1, wherein the aliphatic dicarboxylic acid is selected from the group consisting of adipic acid, sebacic acid, dodecanedioic acid, octadecanedioic acid, C-19 dimer diacid, C-36 dimer diacid and combinations thereof.

8. The method of claim 7, wherein the aliphatic dicarboxylic acid is dodecanedioic acid.

9. The method of claim 1, wherein the diaryl carbonate is diphenyl carbonate.

10. A method according to claim 1 wherein said reacting is carried out at a temperature between about 180 and about 225° C.

* * * * *